United States Patent
Berlinger et al.

(10) Patent No.: US 10,780,297 B2
(45) Date of Patent: Sep. 22, 2020

(54) SORTING THE SEQUENTIAL ARRANGEMENT OF RADIATION TREATMENT BEAMS REGARDING WELL-DISTRIBUTED UNOBSTRUCTED LINES OF SIGHT

(71) Applicant: Brainlab AG, Munich (DE)

(72) Inventors: Kajetan Berlinger, Munich (DE); Hagen Kaiser, Icking (DE)

(73) Assignee: BRAINLAB AG, Munich (DE)

( * ) Notice: Subject to any disclaimer, the term of this patent is extended or adjusted under 35 U.S.C. 154(b) by 0 days.

(21) Appl. No.: 15/564,600

(22) PCT Filed: Feb. 10, 2017

(86) PCT No.: PCT/EP2017/052940
§ 371 (c)(1),
(2) Date: Oct. 5, 2017

(87) PCT Pub. No.: WO2017/137527
PCT Pub. Date: Aug. 17, 2017

(65) Prior Publication Data
US 2018/0093110 A1    Apr. 5, 2018

(30) Foreign Application Priority Data
Feb. 10, 2016  (WO) .................. PCT/EP2016/052840

(51) Int. Cl.
*A61N 5/10*   (2006.01)
*G16H 20/40*  (2018.01)
(Continued)

(52) U.S. Cl.
CPC ......... *A61N 5/1049* (2013.01); *A61N 5/1064* (2013.01); *A61N 5/1069* (2013.01);
(Continued)

(58) Field of Classification Search
None
See application file for complete search history.

(56) References Cited

U.S. PATENT DOCUMENTS 7,046,762 B2 * 5/2006 Lee .................. A61N 5/1031
378/65
8,086,004 B2 12/2011 Kuduvalli et al.
(Continued)

FOREIGN PATENT DOCUMENTS

EP        2159725 A1    3/2010

OTHER PUBLICATIONS

Pugachev et al., "Beam orientation optimization in intensity-modulated radiation treatment planning", Med. Phys. 27(6), 2000, pp. 1238-1245.*
(Continued)

*Primary Examiner* — Katherine L Fernandez
*Assistant Examiner* — Yi-Shan Yang
(74) *Attorney, Agent, or Firm* — Tucker Ellis LLP

(57) ABSTRACT

Disclosed is a method for determining a positional pattern of an irradiation unit for irradiating a patient with treatment radiation. Optimal order data describing an order of the irradiation unit positions for which the statistical value is optimal is determined. The optimal order data is determined based on irradiation unit position data describing irradiation unit positions of the irradiation unit for which the imaging device has a free viewing direction onto the position of the patient, position orders data describing all possible orders of the irradiation unit positions for which the imaging device has a free viewing direction onto the position of the patient, and intersection angle data describing a statistical quantity of the intersection angles between free viewing directions of (Continued)

the imaging unit for irradiation unit positions which are immediately subsequent in the order described by the position orders data.

18 Claims, 5 Drawing Sheets

(51) Int. Cl.
    *G06T 7/80*     (2017.01)
    *G06T 7/77*     (2017.01)
    *G06T 7/00*     (2017.01)
    *G06T 1/00*     (2006.01)

(52) U.S. Cl.
    CPC ............... *G06T 1/0007* (2013.01); *G06T 7/77* (2017.01); *G06T 7/80* (2017.01); *G06T 7/97* (2017.01); *G16H 20/40* (2018.01); *A61N 2005/1059* (2013.01); *G06T 2207/10116* (2013.01)

(56) References Cited

U.S. PATENT DOCUMENTS

| | | | |
|---|---|---|---|
| 2007/0003007 A1* | 1/2007 | Carrano | A61B 6/022 378/41 |
| 2010/0086183 A1* | 4/2010 | Vik | A61N 5/1031 382/128 |
| 2011/0080990 A1 | 4/2011 | Filiberti et al. | |
| 2017/0216632 A1* | 8/2017 | Lee | A61N 5/1081 |

OTHER PUBLICATIONS

European Patent Office, International Search Report and Written Opinion corresponding to PCT/EP2017/052940, dated May 4, 2017, pp. 1-15.

Justus Adamson et al, Optimizing Monoscopic kV Fluoro Acquisition for Prostate Intrafaction Motion Evaluation, NIH—Public Acess, Author Manuscript, Phys Med Bio. available in PMC 2009 May 2013, pp. 1-25. USA.

\* cited by examiner

SORTING THE SEQUENTIAL ARRANGEMENT OF RADIATION TREATMENT BEAMS REGARDING WELL-DISTRIBUTED UNOBSTRUCTED LINES OF SIGHT

The present invention relates to a computer-implemented method for determining a positional pattern of an irradiation unit for irradiating a patient with treatment radiation, a corresponding computer program, a non-transitory program storage medium storing such a program and a computer for executing the program, as well as a system for determining a positional pattern of an irradiation unit for irradiating a patient with treatment radiation, the system comprising an electronic data storage device and such a computer. The invention also relates to a radiation treatment system comprising: an irradiation treatment device comprising an irradiation unit and an imaging device and the aforementioned computer.

TECHNICAL BACKGROUND

So far the treatment beams defined in a radiotherapy/radiosurgery treatment plan are processed in an order guaranteeing short travels for the gantry of the irradiation unit, and thereby maybe guaranteeing shorter treatment times. However, many camera systems suffer from the gantry obstructing one of the camera's lines of sight depending on the gantry angle. Thus, driving the irradiation unit of a treatment device to the positions for emitting the treatment beams in a time-optimised manner may lead to undesirable obstruction of the beam path (the line of sight between the treatment device and the position of the patient) specifically by constituents of the treatment device (such as the gantry).

The present invention allows for determining a sequence of positions of the irradiation unit which avoids such an obstruction.

Aspects of the present invention, examples and exemplary steps and their embodiments are disclosed in the following. Different exemplary features of the invention can be combined in accordance with the invention wherever technically expedient and feasible.

Exemplary Short Description of the Present Invention

In the following, a short description of the specific features of the present invention is given which shall not be understood to limit the invention only to the features or a combination of the features described in this section.

The disclosed method encompasses determining an optimal order of positions of the gantry of a radiotherapy/radiosurgery device so that for positions which are adjacent in that order images can be taken of the patient's body which allow for an improved reconstruction of stereo images or pseudo-stereo images of the patient's body which are used for assessing whether the patient is placed relative to the gantry as desired (and/or as prescribed by a treatment plan). The optimal order is determined such that the stereo-imaging field of view achievable for gantry positions neighbouring each other in the optimised order is maximised e.g. on average.

General Description of the Present Invention

In this section, a description of the general features of the present invention is given for example by referring to possible embodiments of the invention.

The disclosed method provides, in a first aspect, a computer-implemented method for determining a positional pattern of an irradiation unit for irradiating a patient with treatment radiation, the irradiation unit being part of an irradiation treatment device having an imaging device for generating a medical image of the patient. The method comprises executing, on at least one processor of at least one computer, the following exemplary steps which are executed by the at least one processor.

In a (for example first) exemplary step, irradiation unit position data is acquired which describes (for example, defines) irradiation unit positions of the irradiation unit for which the imaging device has a free viewing direction onto the position of the patient. The free viewing direction is a free line of sight from the imaging device to the position of the patient. Specifically, the free line of sight is not impeded by a part of the irradiation unit (such as the gantry of the irradiation unit which constitutes an emitting end at which the treatment beam is emitted from the irradiating unit). The imaging device may be an x-ray imaging device. The imaging device can be at least one of an imaging device having (for example exactly) two imaging units such as a stereo imaging device (for example, an infrared-sensitive imaging device like a stereo thermal camera such as a stereo infrared-sensitive camera, or a stereo x-ray camera, specifically an x-ray imaging device having two imaging units such as each a flat panel x-ray emitter/detector combination which in one example has a fixed position relative to the patient during the imaging process—and in another example may have a variable position relative to the patient during the imaging process, a range camera or camera for measuring distance on the basis of detecting reflections of structured light from the surface of the patient's body) and an imaging device having (for example only) a single imaging unit (for example, an infrared-sensitive imaging device like a mono thermal camera or an x-ray imaging device having only a single imaging unit, such as a single x-ray emitter/detector combination with a variable position relative to the patient during the imaging process). In one example embodiment, the imaging device comprises at least two imaging units (for example, two flat panel x-ray emitter/detector combinations which constitute a stereo x-ray camera) and the irradiation unit positions are positions of the irradiation unit for which the only one or all of the at least two imaging units have a free viewing direction.

In one example embodiment of this step, the irradiation unit position data is predetermined and has been generated on the basis of treatment plan data which describes (for example, defines) an irradiation treatment plan. The irradiation treatment plan defines for example treatment positions which are relative positions between the irradiation treatment device and a treatment body part of the patient at which the treatment radiation shall be emitted. The treatment data is in one example predetermined (i.e. has already been determined, specifically determining (e.g. calculating) the irradiation treatment plan is not part of the disclosed method.

In another example embodiment of this step, irradiation unit position data is predetermined and has been generated on the basis of device geometry data describing an operational geometry of the irradiation treatment device, for example the relative position between the irradiation unit and the viewing direction. The irradiation unit position data may therefore be defined by the irradiation treatment device In a (for example second) exemplary step, position orders data is determined which describes (for example, defines) all possible orders of the irradiation unit positions for which the imaging device has a free viewing direction onto the position of the patient. The position orders data is determined based on the irradiation unit position data. Determining the position orders data encompasses calculating all possible sequences of irradiation unit positions which are associated with a free viewing direction of the imaging device onto the position of the patient. The order or sequence, respectively, of the irradiation unit positions is an order in time and space and defines an order in which the irradiation unit shall attain the irradiation unit positions. The order is discrete in the sense that it contains only discrete individual positions which need not necessarily be adjacent (neighbouring) in space. Any wording herein referring to adjacent and/or subsequent and/or neighbouring irradiation unit positions means that they are adjacent and/or subsequent and/or neighbouring only with regard to their location in the order/sequence of irradiation unit positions and not necessarily in real space.

In a (for example third) exemplary step, intersection angle data is determined which describes (for example, defines) a statistical quantity (for example, a sum, the average or an average field of view) of the intersection angles between free viewing directions of the imaging unit for irradiation unit positions which are immediately subsequent (i.e. neighbouring) in the order described by the position orders data. The intersection angle data is determined based on the irradiation unit position data and the position orders data. For example, the intersection angle data is determined per order (i.e. per ordered sequence), for example for each order, defined by the position orders data. The intersection angles between viewing directions define a field of view of the imaging device between the pairwise subsequent irradiation unit positions. For example, the intersection angles define the extent (i.e. an outer boundary in a two-dimensional projection) of the field of view of the imaging device between the pairwise subsequent irradiation unit positions. In example embodiments of this step, the statistical quantity may be at least one of a sum of the intersection angles, the average of the intersection angles, or the average field of view of the imaging unit between the viewing directions associated with the intersection angles. The intersection angles in one example embodiment of this step consist (for example exclusively) of obtuse angles and right angles or of (for example exclusively) acute angles and right angles.

In a (for example fourth) exemplary step, optimal order data is determined which describes (for example, defines) an order of the irradiation unit positions for which the statistical value is optimal. The optimal order data is determined based on the intersection angle data and the position orders data. The optimal order is an order for which the statistical quantity is a maximum (specifically, attains a maximum value). The optimal order can then be stored for later use as an order of positions which the irradiation unit is controlled to attain for example for conducting radiotherapy on the patient. If more than one order of the irradiation unit position is associated with an optimum of the statistical quantity, the order of the irradiation unit positions associated with the smallest standard deviation is determined as the optimal order. If more than one order of the irradiation unit position is associated with a smallest standard deviation, the order of the irradiation unit positions associated with the smallest amount of time for moving the irradiation unit through the order of irradiation unit positions is determined as the optimal order. The optimisation of the order of the irradiation unit positions is effected by finding those positions for which the viewing direction is not obscured (for the case of an imaging device having only a single imaging unit, this step is optional, as will be clear to the skilled person e.g. from FIG. 2 which shows that no irradiation unit position is obscured in that case), and then putting them in such an order that e.g. on average the intersection angle between non-obscured viewing directions (free lines of sight) associated with adjacent/subsequent irradiation unit positions is maximized.

The maximisation may additionally or alternatively be achieved by applying an optimisation algorithm such as the one disclosed in the following to the sequence of irradiation unit positions in order to optimise the statistical measure (e.g. maximising the average intersection angle).

For each permutation of irradiation unit positions, it is determined whether it constitutes an acceptable order of the irradiation unit positions according to a predetermined (predefined) acceptance criterion. If an order is determined to be acceptable, the optimisation procedure ends and analysis of further permutations can be avoided, whereby the computational efficiency of the optimisation procedure is increased compared to a brute force approach which would include all possible permutations are analysed as to their suitability. The acceptance criterion is in one example of this approach defined as a combination of the average intersection angle of viewing directions (AVG) (either as absolute value or as a percentage of the range from the smallest intersection angle to the largest intersection angle in one permutation) and the standard deviation (SD) associated therewith for each permutation of irradiation unit positions to be analysed. The following pseudocode example uses an average intersection angle of greater than or equal to 60° in absolute value or an average intersection angle of greater than or equal to 70% the range in a relative definition, each at an associated standard deviation of less than or equal to 10°:

```
currentSequenceOfBeams={TreatmentBeamAngle1, TreatmentBeamAngle2, . . . , TreatmentBeamAngleN};
Range=Max(currentSequenceOfBeams)−Min(currentSequenceOf Beams); // Compute Range between maximum and minimum intersection angle
int n=size(currentSequenceOfBeams);
int i=0;
Termination=false;
Repeat:
   i++;
   computeAVGandSD(currentSequenceOf Beams)=>AVG
      and SD; // Compute average (e.g. the arithmetic mean
      value) of acute intersection angles and the associated
      standard deviation for currentSequenceOfBeams
   If ((AVG>=60°) && (SD<=10°))
      Termination=true;
   Else If ((AVG>=70%*Range) && (SD<=10°))
      Termination=true;
   Else    computeNextPermutation(currentSequenceOf
      Beams); // this may result in a change to currentSequenceOfBeams like={beam2, beam1, . . . , beamN}
Until (i>=n!||Termination==true) // acceptance criterion for
currentSequenceOfBeams
```

The meaning of the variables used in the above pseudocode is as follows:
currentSequenceOfBeams: represents an input (reading) of the unordered sequence of beam directions/irradiation unit positions and/or intersection angles TreatmentBeamAnglei (i=1, 2, . . . , N);
Range: angular value representing the difference between the largest value in currentSequenceOf Beams to the smallest value in currentSequenceOfBeams.

The meaning of operators in the above pseudocode is as follows:
>=: greater than or equal to;
<=: less than or equal to;
*: multiplication;
=: set to;

&&: logical "AND";
==: identical to (for Boolean variables);
!: factorial;
||: logical "OR".
// indicates the beginning of a comment on a code line.

If the imaging device comprises at least two imaging units, the disclosed method may comprise determining, based on the irradiation unit position data, stereo-imaging data describing (for example, defining) irradiation unit positions for which all of the at least two imaging units have a free viewing direction. The optimal order data may then be determined based on the stereo-imaging data, for example by preferring orders described by the position order data having a maximum of irradiation unit positions for which all of the at least two imaging units have a free viewing direction for determining the optimal order data. Also, imaging unit control data may be determined based on the irradiation unit position data. The imaging unit control data describes (for example defines) a control signal for controlling only the at least one of the at least two imaging units which has a free viewing direction to take an image.

In a second aspect, the disclosed method relates to a computer-implemented medical data processing method for determining a positional pattern of an irradiation unit for irradiating a patient with treatment radiation, the irradiation unit being part of an irradiation treatment device having an imaging device having two imaging units for generating a medical image of the patient, the method comprising executing, on at least one processor of at least one computer, steps of:

a) acquiring, at the at least one processor, irradiation unit position data describing irradiation unit positions of the irradiation unit for which the imaging device has a free viewing direction onto the position of the patient which is a free line of sight from at least one of the imaging units to the position of the patient;

b) determining, by the at least one processor and based on the irradiation unit position data, irradiation unit control data describing control signals for controlling the irradiation unit to alternately attain irradiation unit positions described by the irradiation unit position data, wherein the free line of sight of each a different one of the two imaging units is impeded by at least part of the irradiation unit in two immediately subsequently attained irradiation unit positions.

The terminology used above for defining the second aspect is defined and to be understood like the terminology used for describing the first aspect.

In a third aspect, the disclosed method relates to controlling the position of an irradiation unit of an irradiation treatment device, the method comprising executing, on at least one processor of at least one computer, steps of:

executing the method according to any of the first or second aspects; and issuing, by the at least one processor and to the irradiation treatment device and based on the optimal order data, control signal data for controlling the imaging unit to attain the imaging positions in the order described by the optimal order data.

In a fourth aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first, second or third aspects.

In a fifth aspect, the invention is directed to a non-transitory computer-readable program storage medium on which the program according to the fourth aspect is stored.

In a sixth aspect, the invention is directed to at least one computer (for example, a computer), comprising at least one processor (for example, a processor) and at least one memory (for example, a memory), wherein the program according to the fourth aspect is running on the processor or is loaded into the memory, or wherein the at least one computer comprises the program storage medium according to the fifth aspect.

In a seventh aspect, the invention is directed to a system for determining a positional pattern of an irradiation unit for irradiating a patient with treatment radiation, the system comprising:

a) the at least one computer according to the sixth aspect; and b) at least one electronic data storage device storing the irradiation unit position data and, as far as the irradiation unit position data is predetermined and has been generated on the basis of treatment plan data, the treatment plan data, wherein the at least one computer is operably coupled to the at least one electronic data storage device for acquiring, from the at least one electronic data storage device, the irradiation unit position data and, if the electronic data storage device stores the treatment plan data, the treatment plan data.

In an eighth aspect, the invention is directed to a radiation treatment system, comprising:

an irradiation treatment device comprising an irradiation unit and an imaging device; and the at least one computer according to the sixth aspect or the system according to the seventh aspect, wherein the at least one computer is operatively coupled to the irradiation treatment device for controlling the position of at least the irradiation unit on the basis of the optimal order data.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The information on the imaging geometry preferably comprises information which allows the analysis image (x-ray image) to be calculated, given a known relative position between the imaging geometry analysis apparatus and the analysis object (anatomical body part) to be analysed by x-ray radiation, if the analysis object which is to be analysed is known, wherein "known" means that the spatial geometry (size and shape) of the analysis object is known. This means for example that three-dimensional, "spatially resolved" information concerning the interaction between the analysis object (anatomical body part) and the analysis radiation (x-ray radiation) is known, wherein "interaction" means for example that the analysis radiation is blocked or partially or completely allowed to pass by the analysis object. The location and in particular orientation of the imaging geometry is for example defined by the position of the x-ray device, for example by the position of the x-ray source and the x-ray detector and/or for example by the position of the multiplicity (manifold) of x-ray beams which pass through the analysis object and are detected by the x-ray detector. The imaging geometry for example describes the position (i.e. the location and in particular the orientation) and the shape (for example, a conical shape exhibiting a specific angle of inclination) of said multiplicity (manifold). The position can for example be represented by the position of an x-ray beam which passes through the centre of said multiplicity or by the position of a geometric object (such as a truncated cone) which represents the multiplicity (manifold) of x-ray beams. Information concerning the above-mentioned interaction is preferably known in three dimensions, for example from a three-dimensional CT, and describes the interaction in a spatially resolved way for points and/or regions of the analysis object, for example for all of the points and/or regions of the analysis object. Knowledge of the imaging geometry for example allows the location of a source of the radiation (for example, an x-ray source) to be calculated relative to an image plane (for example, the plane of an x-ray detector). With respect to the connection between three-dimensional analysis objects and two-dimensional analysis images as defined by the imaging geometry, reference is made for example to the following publications:

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/healthcare_us_elekta_v-mat.php and http://www.varian.com/us/oncology/treatments/treatment_techniques/rapidarc.

A treatment body part can be treated by one or more treatment beams issued from one or more directions at one or more times. The treatment by means of the at least one treatment beam thus follows a particular spatial and temporal pattern. The term "beam arrangement" is then used to cover the spatial and temporal features of the treatment by means of the at least one treatment beam. The beam arrangement is an arrangement of at least one treatment beam.

The "beam positions" describe the positions of the treatment beams of the beam arrangement. The arrangement of beam positions is referred to as the positional arrangement. A beam position is preferably defined by the beam direction and additional information which allows a specific location, for example in three-dimensional space, to be assigned to the treatment beam, for example information about its co-ordinates in a defined co-ordinate system. The specific location is a point, preferably a point on a straight line. This line is then referred to as a "beam line" and extends in the beam direction, for example along the central axis of the treatment beam. The defined co-ordinate system is preferably defined relative to a treatment device (also called irradiation treatment device) which emits the treatment beam(s) or relative to at least a part of the patient's body. The positional arrangement comprises and for example consists of at least one beam position, for example a discrete set of beam positions (for example, two or more different beam positions), or a continuous multiplicity (manifold) of beam positions.

For example, one or more treatment beams adopt(s) the treatment beam position(s) defined by the positional arrangement simultaneously or sequentially during treatment (for example sequentially if there is only one beam source to emit a treatment beam). If there are several beam sources, it is also possible for at least a subset of the beam positions to be adopted simultaneously by treatment beams during the treatment. For example, one or more subsets of the treatment beams can adopt the beam positions of the positional arrangement in accordance with a predefined sequence. A subset of treatment beams comprises one or more treatment beams. The complete set of treatment beams which comprises one or more treatment beams which adopt(s) all the beam positions defined by the positional arrangement is then the beam arrangement.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

DESCRIPTION OF THE FIGURES

In the following, the invention is described with reference to the appended figures which represent a specific embodiment of the invention. The scope of the invention is however not limited to the specific features disclosed in the context of the figures, wherein.

Figure 1:
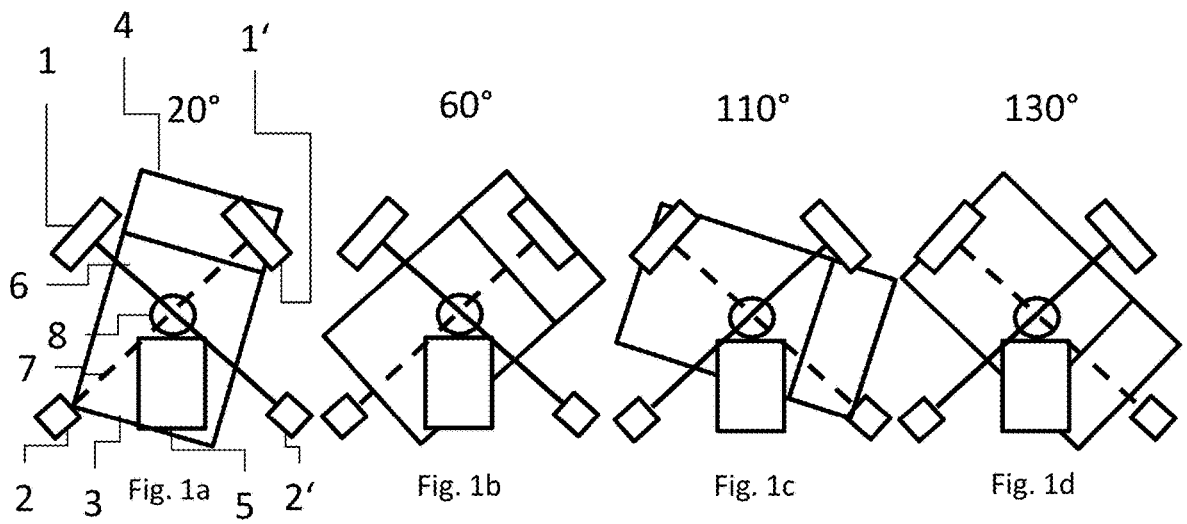
FIGS. 1a to 1d show a prior art method of controlling the gantry of the irradiation unit for the case of a stereo camera as an imaging device.
FIGS. 1e to 1h show application of the disclosed method to the case of FIGS. 1a to 1d.
FIGS. 1i and 1j show the resulting intersection (reconstruction) angles for the irradiation unit positions of FIGS. 1a to 1h and 1e to 1h, respectively.
Figure 1:
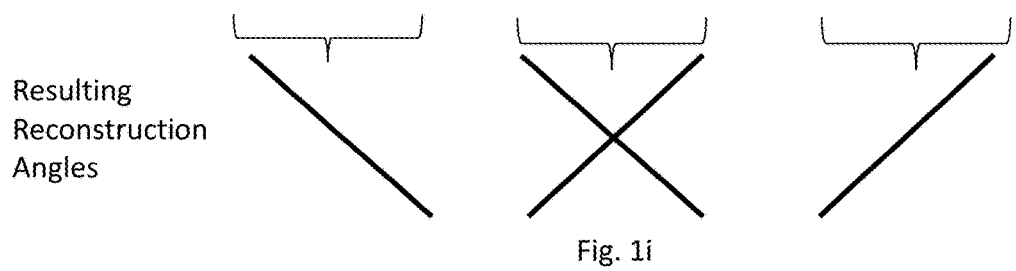
Figure 1:
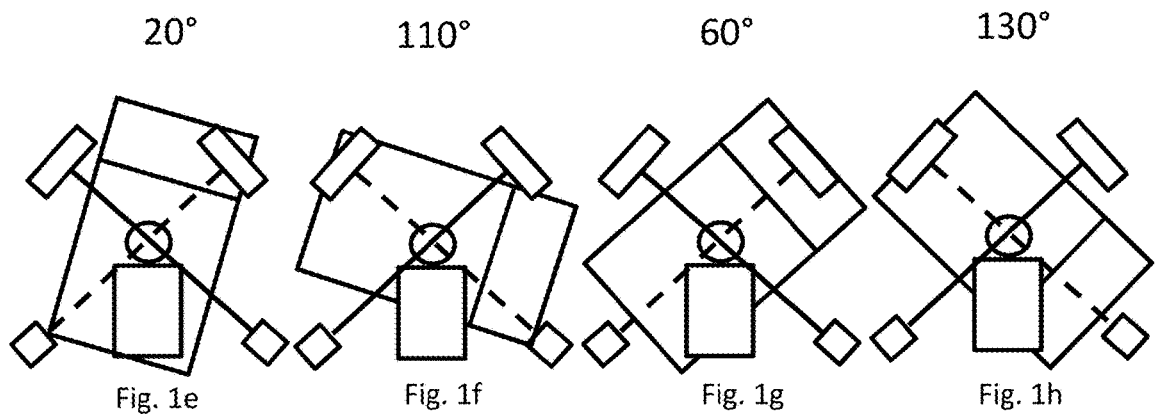
Figure 1:
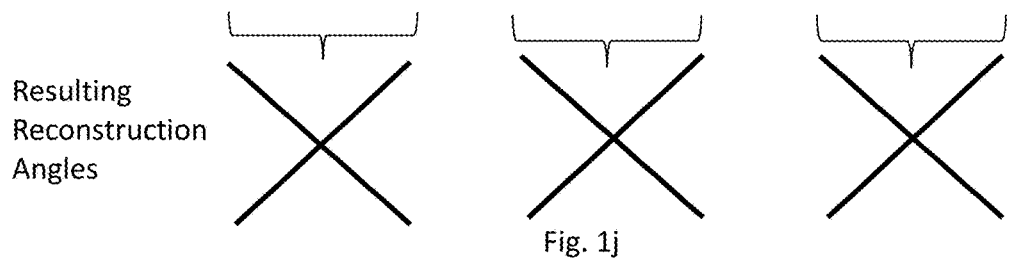

Throughout the figures, dashed lines indicating viewing directions (e.g. viewing directions 6, 7) indicate an obscured viewing direction, and solid lines indicating viewing directions (e.g. viewing directions 6, 7) indicate a free (non-obscured) viewing direction. The same reference signs have the same meaning throughout the figures.

FIGS. 1a to 1d illustrate a sequence of gantry positions (indicated by the amount of degrees resembling the rotational phase of the gantry shown above each sub-figure) of a gantry 4 of an irradiation treatment device 3 having a couch 5 for placing a patient 8 onto. Lines 6 and 7 indicate the viewing directions from x-ray emitters 2, 2' to flat panel x-ray detectors 1, 1' of a stereo x-ray camera being the imaging device (each pair of emitters 2, 2' and detectors 1, 1' forming each one imaging unit). As can be seen in FIGS. 1a to 1d, the viewing direction of one of the imaging unit is always blocked by the gantry 4 in each of the positions shown. Thus, subsequent imaging positions do not allow reconstructing stereo-view images from a series of images taken when the gantry is in the positions (irradiation unit positions) shown in FIGS. 1a to 1d. The order of irradiation unit positions shown in FIGS. 1a to 1d is designed to minimize the travel time of the gantry 4 when going through that ordered sequence of irradiation unit positions.

FIGS. 1e to 1h show a re-sorting of the irradiation unit positions so that each a different viewing direction between alternating pairs of emitters 2, 2' and detectors 1, 1' (i.e. the viewing direction of each a different one of the imaging unit for subsequent images of the sequence) is obscured, thus allowing reconstructing of stereo-view images from pairs of images taken for subsequent irradiation unit positions: for example, one stereo image can be reconstructed from the individual images taken in the irradiation unit positions at 20° and 110° shown in FIGS. 1e and 1f, one stereo image can be reconstructed from the individual images taken in the irradiation unit positions at 110° and 60° shown in FIGS. 1f and 1g, and one stereo image can be reconstructed from the individual images taken in the irradiation unit positions at 60° an 130° shown in FIGS. 1g and 1h. Throughout FIGS. 1 1i and 1j, the straight lines titled "resulting reconstruction angles" illustrate the intersecting viewing direction associated with subsequent irradiation unit positions of FIGS. 1a to 1d and 1e to 1h, respectively.

Figure 3:
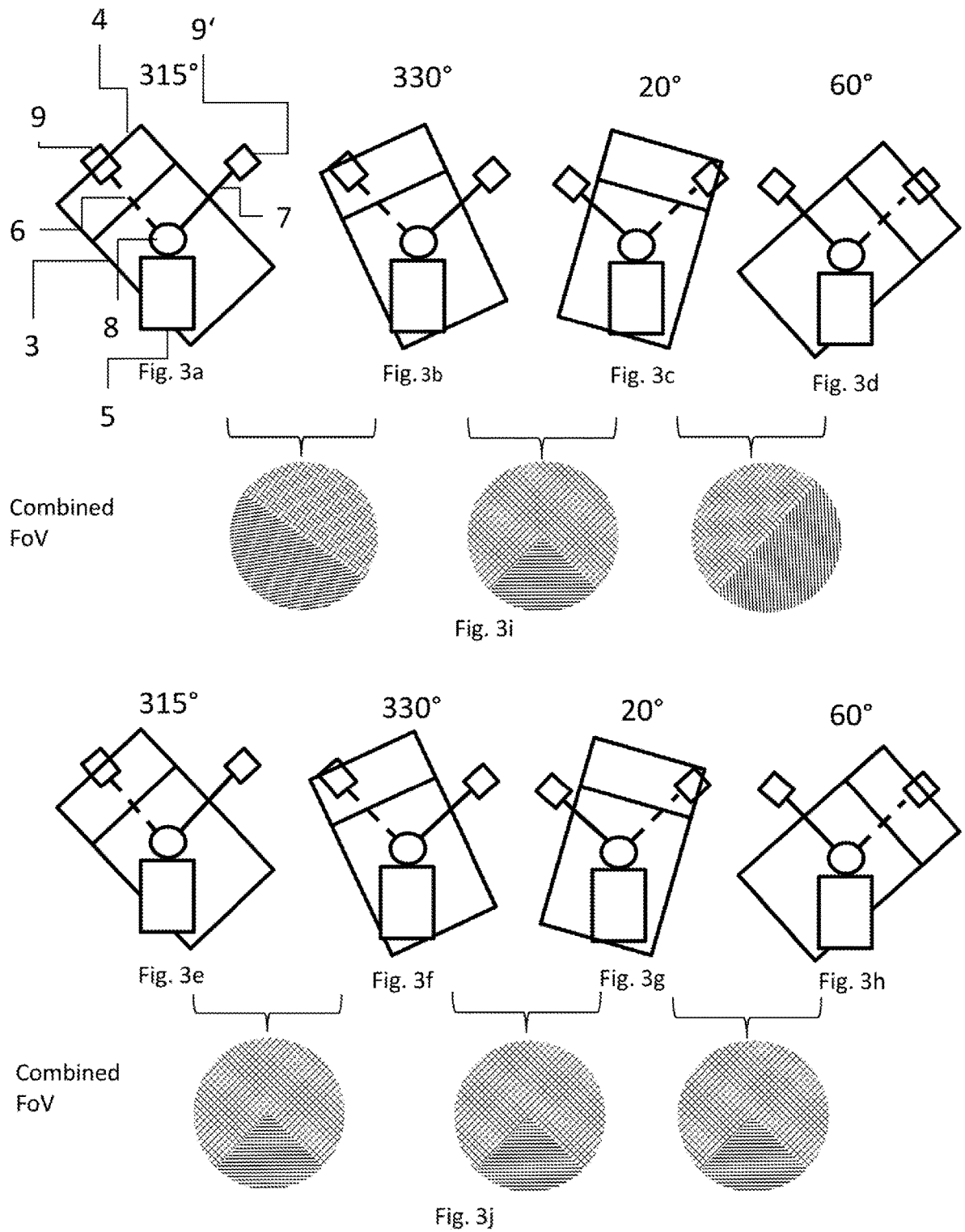
FIGS. 3a to 3d show the combined field of view attributable to subsequent gantry positions for the case of using a thermal camera as the imaging device in an unordered sequence of gantry positions.
FIGS. 3e to 3h show the combined field of view attributable to subsequent gantry positions for the case of using a thermal camera as the imaging device in an optimized sequence of gantry positions.
FIGS. 3i and 3j show the combined field of view associated with the irradiation unit positions of FIGS. 3a to 3d and 3e to 3h, respectively.

Throughout FIG. 3, the circular diagram represents a mapping of the field of view onto a section through patient's body, wherein the crossed shading indicates the combined field of view of the adjacent irradiation unit positions, and the linear shading indicates the spatial sector which is not visible even after combination of the images taken at two adjacent irradiation unit positions.

FIGS. 2a to 2l illustrate the difference between the disclosed method and the state of the art for the case of an imaging device having only a single imaging unit comprising one x-ray emitter unit 11 and one x-ray detector unit 22. Throughout FIGS. 2m, 2n and 2o, the straight lines titled "resulting reconstruction angles" illustrate the intersecting viewing direction associated with subsequent irradiation unit positions of FIGS. 2a to 2d, 2e to 2h and 2i to 2l, respectively. Compared to the prior art sequence of FIGS. 2a to 2d which again seeks to minimize the travel time of the gantry 4, the disclosed method changes the order of irradiation unit positions for taking images with the single imaging unit to follow the sequences shown in FIGS. 2e to 2h or 2i to 2l, respectively. The latter two sequences are determined such that an intersection angle between viewing directions 8 associated with immediately subsequent (adjacent) irradiation unit positions (and therefore in the case of FIG. 2 also subsequent positions of the viewing direction relative to the patient place on the couch 5, and the combined field of view) is on average maximized and enlarged (see also the representation of intersecting viewing directions 8 between the adjacent figures) compared to the prior art case of FIGS. 2a to 2d. This supports easier and more reliable fusion of subsequent images so that the reconstruction of stereo images is improved. Both ordered sequences of FIGS. 2e to 2h and 2i to 2l have a higher average combined field of view than the sequence of FIGS. 2a to 2d, but the sequence of FIGS. 2i to 2l is associated with a smaller standard deviation of the intersection angle and therefore selected as the optimal order of the irradiation unit positions, if the combined field of view FIGS. 2i to 2l is the same as the combined field of view of FIGS. 2e to 2h.

FIG. 3 illustrates application of the disclosed method to the case of the imaging device being a stereo thermal camera having two infrared-sensitive imaging units 9, 9'. FIGS. 3e to 3h illustrate that the combined field of view (FoV) achievable by combining (e.g. fusing) subsequent images taken by the two imaging units 9, 9' by optimizing their order is on average enlarged (crossed shading in the circle shown in FIG. 3j and surrounding the intersecting subsequent viewing directions 6, 7) when applying the disclosed method (refer to FIGS. 3e to 3h and 3j) compared to the prior art order of irradiation unit positions (refer to FIGS. 3a to 3d and 3i). The linear shading in the circles of FIGS. 3i and 3j indicate the angular range which is obscured and cannot be viewed and/or imaged for a combination of subsequent imaging positions sown in FIGS. 3a to 3d and 3e to 3h, respectively. Note that for application of a stereo thermal camera as shown in FIG. 3, the number of irradiation unit positions associated with an obscured viewing direction 6, 7 is decreased by 50% compared to the case of FIGS. 1 and 2 in which x-ray-based imaging devices are used, because the patient is imaged only from one hemisphere in three-dimensional space.

Figure 4:
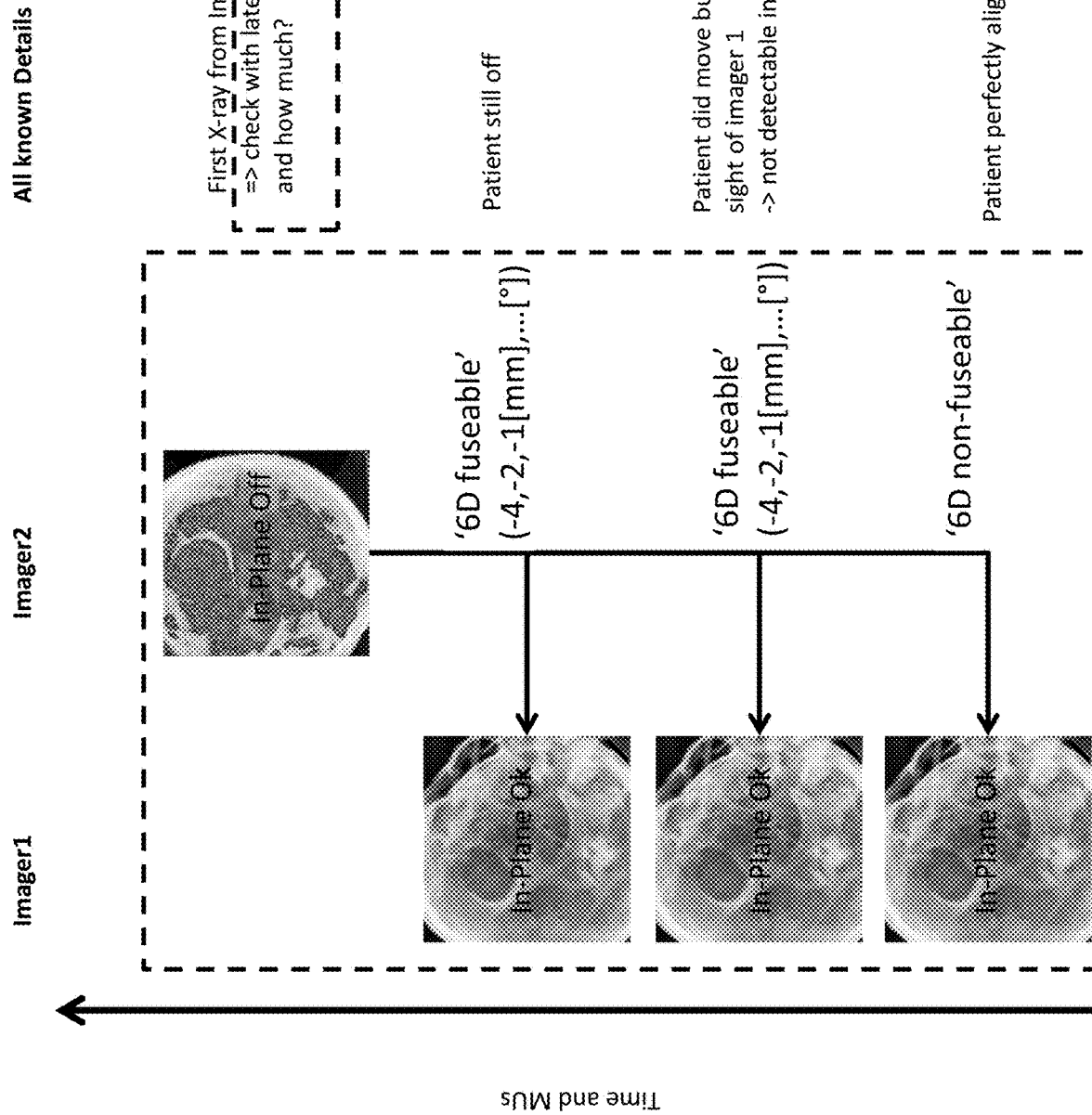
FIG. 4 shows application information derivable from fusion of images in six degrees of freedom, the images having been taken by the imaging device.

FIG. 4 shows the information derivable from fused stereo images taken by two different imaging units (Imager1 and Imager2). An example of such information is knowledge that the patient is off the desired irradiation position relative to the irradiation unit by a certain amount in e.g. three coordinates, or that the irradiation unit and the patient are perfectly aligned.

When having only one X-ray image of the scene for image position verification, an in-plane two-dimensional fusion only may be performed. In doing so, no positional information is retrieved and it is only checked whether the in-plane shift is within a certain tolerance. Using the disclosed method, the latest image from the other—possibly obstructed view—can be used in combination with the live X-ray image (non-obstructed) to perform a six-dimensional (three translational degrees of freedom, three rotational degrees of freedom) fusion. Visual inspection of this six-dimensional fusion result yields whether the stereo image pair was taken at the same position of the patient. If so, the following can be determined:

a) a quantified offset in 6D (six degrees of freedom, namely three translational degrees of freedom and three rotational degrees of freedom); and b) the point in time the error was introduced.

If for instance the error was already introduced when using Imager1 but in the line of sight of Imager1, it can be determined when this error was introduced by combining the just acquired X-ray from Imager2 with the latest images from Imager1. The image pair that is not combinable (because it showed a different position of the patient) determines the point in time. The thereby gained information can answer questions like: Shall I continue treatment? What do I have to take into account for the next treatment plan (OARs, Target doses etc. . . . )?

An example algorithm for the disclosed method when having non-static camera setup is:

1) Make a list of all viewing directions that have clear line of sight

2) Generate all possible combinations/orderings for these viewing directions

3) Compute for all orderings the sum of the (acute-angled) intersection angles of two consecutive viewing angles 4) Determine which ordering provides the maximum of this summation 5) In case there is more than one solution, take the one providing the smaller standard deviation 6) In case there is still more than one solution, take the solution that is easier for the operator (reduces gantry travelling time)

Figure 2:
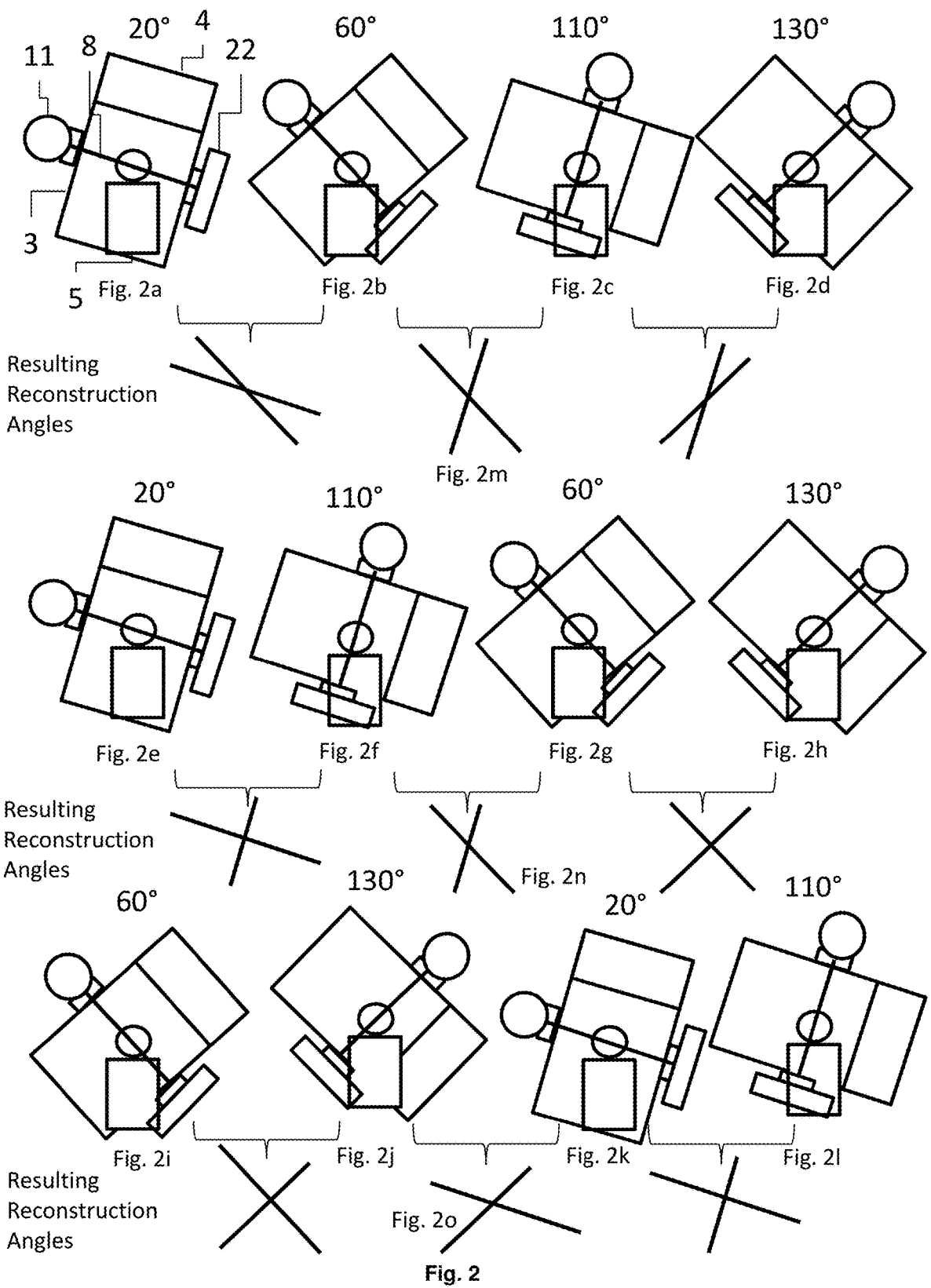
FIGS. 2a to 2d show a prior art method of controlling the gantry of the irradiation unit for the case of an imaging device comprising only one imaging unit.
FIGS. 2e to 2l show application of the disclosed method to the case of FIGS. 2a to 2d.
FIGS. 2m to 2o show the resulting intersection (reconstruction) angles for the irradiation unit positions of FIGS. 2a to 2d and 2e to 2h and 2i to 2l, respectively.
Figure 5:
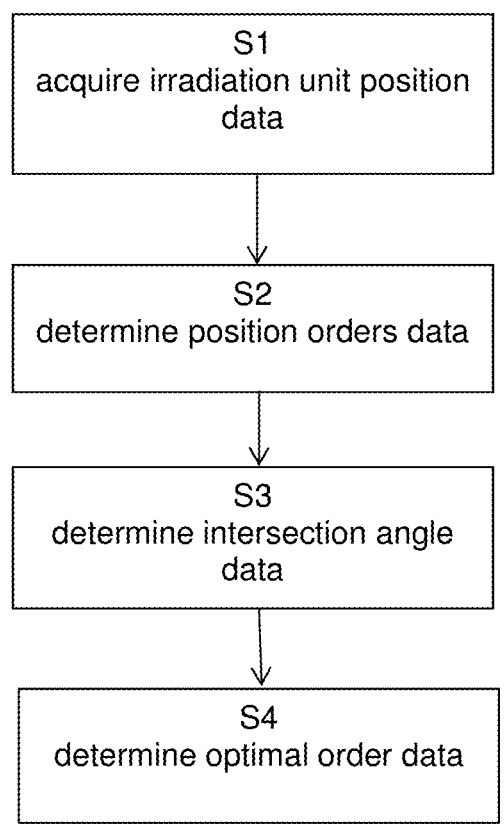
FIG. 5 illustrates a flow diagram representing basic steps of the disclosed method.

FIG. 5 is a flow diagram illustrating the basic steps of the disclosed method which in the illustrative example of FIG. 5 starts with a step S1 of acquiring irradiation unit position data, corresponding to determining gantry angles in FIGS. 1, 2 and 3 which are associated with a free line of sight. In subsequent step S2, the position orders data is determined so as to achieve an ordering of the gantry positions as shown in FIGS. 1e to 1 h and 3e to 3h, respectively, and 2e to 2h or 2i to 2l. This is followed by step S3 in which the intersection angle data is determined to assess e.g. the average field of view and—if necessary to achieve a unique result—the standard deviation associated with the field of view for subsequent irradiation unit positions. In step S4, the optimal order data is then determined as described above.

The invention claimed is:

1. A method for determining a positional pattern of an irradiation unit for irradiating a patient with treatment radiation, the irradiation unit being part of an irradiation treatment system including at least one processor, an imaging device for generating a medical image of the patient, and the irradiation unit, the method comprising:

a) acquiring, by the at least one processor, irradiation unit position data describing irradiation unit positions of the irradiation unit for which the imaging device has a free viewing direction onto a position of the patient, wherein the free viewing direction onto the position of the patient is a free line of sight from the imaging device to the position of the patient;

b) determining, by the at least one processor and based on the irradiation unit position data, position orders data describing all possible ordered sequences of the irradiation unit positions described in the irradiation unit position data;

c) determining, by the at least one processor and based on the irradiation unit position data and the position orders data and for each of the possible ordered sequences described by the position orders data, intersection angle data describing a statistical quantity of intersection angles between respective free viewing directions of the imaging device for irradiation unit positions that are neighboring each other in each of the possible ordered sequences described by the position orders data d) determining, by the at least one processor and based on the intersection angle data and the position orders data, optimal order data describing an optimal order, the optimal order being a particular ordered sequence of the irradiation unit positions for which a respective statistical quantity of the particular ordered sequence reaches an optimal predetermined value, or, on a condition that respective statistical quantities of more than one ordered sequence of the irradiation unit positions reach the optimal predetermined value, an ordered sequence, of the more than one ordered sequence having the respective statistical quantities reaching the optimal predetermined value, that satisfies a secondary criterion is determined as the optimal order, wherein, if more than one ordered sequence of the irradiation unit position data satisfy the secondary criterion in addition to reaching the optimal predetermined value, an ordered sequence that further satisfies a tertiary criterion is determined as the optimal order, wherein the tertiary criterion relates to an amount of time for moving the irradiation unit through an order of positions, and wherein the ordered sequence determined as the optimal order satisfies the tertiary criterion when associated with a smallest amount of time for moving through the order of positions; and e) determining, by the at least one processor and based on the optimal order data, control signal data for controlling the imaging unit to attain imaging positions in an order described by the optimal order data.

2. The method according to claim 1, wherein the irradiation unit position data is predetermined and has been generated on a basis of treatment plan data describing an irradiation treatment plan defining treatment positions that are relative positions between the irradiation treatment device and a treatment body part of the patient at which the treatment radiation shall be emitted.

3. The method according to claim 1, wherein the imaging device comprises two imaging units.

4. The method according to claim 3, wherein the two imaging units each are one of an x-ray device, an infrared-sensitive imaging device, or a range camera device.

5. The method according to claim 1, wherein the free line of sight is not impeded by a part of the irradiation unit.

6. The method according to claim 1, wherein the irradiation unit position data is predetermined and has been generated on a basis of device geometry data describing an operational geometry of device components which comprise the irradiation treatment device.

7. The method according to claim 1, wherein the statistical quantity is a sum of the intersection angles, or an average of the intersection angles.

8. The method according to claim 1, wherein the intersection angles consist of obtuse angles and right angles or wherein the intersection angles consist of acute angles and right angles.

9. The method according to claim 1, wherein the intersection angles define a field of view of the imaging device between pairwise adjacent irradiation unit positions.

10. The method according to claim 1, wherein the imaging device comprises at least two imaging units, and wherein the irradiation unit positions are positions of the irradiation unit for which one of the at least two imaging units is unobstructed or wherein the irradiation unit positions are positions of the irradiation unit for which each of the at least two imaging units are unobstructed.

11. The method according to claim 10, comprising:
determining, based on the irradiation unit position data, stereo-imaging data describing the irradiation unit positions for which all of the at least two imaging units are unobstructed, and wherein the optimal order data is determined based on the stereo-imaging data.

12. The method according claim 10, comprising: determining, based on the irradiation unit position data and by the at least one processor, imaging unit control data describing a control signal for controlling only one of the at least two imaging units that is unobstructed to take an image.

13. The method according to claim 1, comprising:
issuing, by the at least one processor, the control signal data for controlling the imaging unit to attain the imaging positions in the order described by the optimal order data; and
controlling, by the at least one processor, the imaging unit according to the control signal data.

14. The method according to claim 1, wherein the secondary criterion relates to a standard deviation of the respective statistical quantity, and wherein an ordered sequence satisfies the secondary criterion when associated with a smallest standard deviation of the respective statistical quantity.

15. A non-transitory computer-readable storage medium having instructions stored thereon, which, when executed by at least one processor of an irradiation treatment system including an irradiation unit for irradiating a patient with treatment radiation and an imaging device for generating a medical image of the patient, causes the at least one processor to perform the steps comprising:

a) acquiring, by the at least one processor, irradiation unit position data describing irradiation unit positions of the irradiation unit for which the imaging device has a free viewing direction onto a position of the patient, wherein the free viewing direction onto the position of the patient is a free line of sight from the imaging device to the position of the patient;

b) determining, by the at least one processor and based on the irradiation unit position data, position orders data describing all possible ordered sequences of the irradiation unit positions described in the irradiation unit position data;

c) determining, by the at least one processor and based on the irradiation unit position data and the position orders data and per each ordered sequence described by the position orders data, intersection angle data describing a statistical quantity of intersection angles between respective free viewing directions of the imaging device for irradiation unit positions that are adjacent to each other in each ordered sequence described by the position orders data;

d) determining, by the at least one processor and based on the intersection angle data and the position orders data, optimal order data describing an optimal order, the optimal order being a particular ordered sequence of the irradiation unit positions for which a respective statistical quantity reaches an optimal predetermined value, or, on a condition that respective statistical quantities of more than one ordered sequence of the irradiation unit positions reach the optimal predetermined value, an ordered sequence, of the more than one ordered sequence having the respective statistical quantities reaching the optimal predetermined value, that also satisfies a secondary criterion is determined as the optimal order, wherein, if more than one ordered sequence of the irradiation unit position data satisfy the secondary criterion in addition to reaching the optimal predetermined value, an ordered sequence that further satisfies a tertiary criterion is determined as the optimal order, wherein the tertiary criterion relates to an amount of time for moving the irradiation unit through an order of positions, and wherein the ordered sequence determined as the optimal order satisfies the tertiary criterion when associated with a smallest amount of time for moving through the order of positions; and e) determining, by the at least one processor and based on the optimal order data, control signal data for controlling the imaging unit to attain imaging positions in an order described by the optimal order data.

16. The non-transitory computer-readable storage medium of claim 15, wherein the instructions cause the at least one processor to perform the additional steps of:

issuing, by the at least one processor, the control signal data for controlling the imaging unit to attain the imaging positions in the order described by the optimal order data; and controlling the imaging unit according to the control signal data.

17. A system for determining a positional pattern of an irradiation unit for irradiating a patient with treatment radiation, the system comprising an irradiation treatment device including, at least one processor, the irradiation unit, and an imaging device for generating a medical image of the patient, wherein the at least one processor is configured to:

a) acquire irradiation unit position data describing irradiation unit positions of the irradiation unit for which the imaging device has a free viewing direction onto a position of the patient, wherein the free viewing direction onto the position of the patient is a free line of sight from the imaging device to the position of the patient;

b) determine, based on the irradiation unit position data, position orders data describing all possible ordered sequences of the irradiation unit positions described in the irradiation unit position data;

c) determine, based on the irradiation unit position data and the position orders data and per each ordered sequence described by the position orders data, intersection angle data describing a statistical quantity of intersection angles between respective free viewing directions of the imaging device for irradiation unit positions that are adjacent to each other in each ordered sequence described by the position orders data;

d) determine, by the at least one processor and based on the intersection angle data and the position orders data, optimal order data describing an optimal order, the optimal order being a particular ordered sequence of the irradiation unit positions for which a respective statistical quantity reaches an optimal predetermined value, or, on a condition that respective statistical quantities of more than one ordered sequence of the irradiation unit positions reach the optimal predetermined value, an ordered sequence, of the more than one ordered sequence having the respective statistical quantities reaching the optimal predetermined value, that satisfies a secondary criterion is determined as the optimal order, wherein, if more than one ordered sequence of the irradiation unit position data satisfy the secondary criterion in addition to reaching the optimal predetermined value, an ordered sequence that further satisfies a tertiary criterion is determined as the optimal order, wherein the tertiary criterion relates to an amount of time for moving the irradiation unit through an order of positions, and wherein the ordered sequence determined as the optimal order satisfies the tertiary criterion when associated with a smallest amount of time for moving through the order of positions; and e) determine, by the at least one processor and based on the optimal order data, control signal data for controlling the imaging unit to attain imaging positions in an order described by the optimal order data.

18. The system of claim 17, wherein the at least one processor is further configured to:

issue the control signal data for controlling the imaging unit to attain the imaging positions in the order described by the optimal order data; and control the imaging unit according to the control signal data.

* * * * *